United States Patent
Miyoshi et al.

(10) Patent No.: US 11,782,325 B1
(45) Date of Patent: Oct. 10, 2023

(54) IMAGE PROCESSING APPARATUS, IMAGE PROCESSING METHOD, AND RECORDING MEDIUM

(71) Applicant: OLYMPUS MEDICAL SYSTEMS CORP., Tokyo (JP)

(72) Inventors: Takashi Miyoshi, Kanagawa (JP); Takuya Matsunaga, Tokyo (JP); Kazuhito Horiuchi, Tokyo (JP); Munenori Fukunishi, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 17/903,117

(22) Filed: Sep. 6, 2022

(51) Int. Cl.
  *G03B 13/36* (2021.01)
  *H04N 23/67* (2023.01)
  *A61B 1/00* (2006.01)

(52) U.S. Cl.
  CPC ............ *G03B 13/36* (2013.01); *H04N 23/67* (2023.01); *A61B 1/00009* (2013.01)

(58) Field of Classification Search
  CPC ..................................................... H04N 23/67
  USPC ........................................................ 348/345
  See application file for complete search history.

(56) References Cited

U.S. PATENT DOCUMENTS

| | | |
|---|---|---|
| 2014/0176692 A1 | 6/2014 | Tsuyuki et al. |
| 2019/0204069 A1* | 7/2019 | Tatsuta ................. G06T 7/0012 |
| 2020/0051261 A1 | 2/2020 | Tsuruyama et al. |

FOREIGN PATENT DOCUMENTS

| | | |
|---|---|---|
| EP | 2 868 254 A1 | 5/2015 |
| EP | 3 513 704 A1 | 7/2019 |
| JP | 5593004 B2 | 9/2014 |
| JP | 2020-024563 A | 2/2020 |
| JP | 2020-124541 A | 8/2020 |

OTHER PUBLICATIONS

Tinghui Zhou, et al.,"Unsupervised Learning of Depth and Ego-Motion from Video", 2017 IEEE Conference on Computer Vision and Pattern Recognition(CVPR), Jul. 21-26, 2017, IEEE.
U.S. Appl. No. 17/903,135.

* cited by examiner

*Primary Examiner* — Joel W Fosselman
(74) *Attorney, Agent, or Firm* — Scully, Scott, Murphy & Presser, P.C.

(57) ABSTRACT

Provided is an image processing apparatus including a processor. The processor is configured to: reconstruct, by employing an image set acquired by means of an endoscope, three-dimensional information of an imaging subject; estimate, by means of an estimator, imaging-subject distances from the image set by employing a learning parameter; calculate, on the basis of the estimated imaging-subject distances and the imaging-subject distances in the three-dimensional information, a scale coefficient; convert relative dimensions of the three-dimensional information to absolute dimensions by employing the scale coefficient; and output the three-dimensional information containing the absolute dimensions. The learning parameter is determined by learning a plurality of learning images including images of imaging-subject distances outside a measurement range in which imaging-subject distances can be measured on the basis of contrast of the image and a position of an autofocus-lens, as well as imaging-subject distances for each of the learning images.

9 Claims, 8 Drawing Sheets

IMAGE PROCESSING APPARATUS, IMAGE PROCESSING METHOD, AND RECORDING MEDIUM

TECHNICAL FIELD

The present invention relates to an image processing apparatus, an image processing method, and a recording medium.

BACKGROUND ART

In the related art, there is a known endoscope having a function for measuring the dimensions of an imaging subject (for example, see Patent Literature 1). In endoscopic examination or endoscopic treatment, it is recommended to change the procedures of polypectomy, EMR/ESD, etc. in accordance with the dimensions of a polyp, and dimensional measurement is effective in making decisions about the procedures. As a means for measuring the dimensions, for example, a stereo optical system or laser light is used. In Patent Literature 1, laser light is radiated onto an imaging subject, and markers for measuring the dimensions of the imaging subject are generated and displayed on the basis of an imaging-subject image in which spots of the laser light are formed.

Meanwhile, in recent years, there have been advances in the development of technologies for generating three-dimensional information of an imaging subject from an image acquired by using a monocular optical system (for example, see Non-Patent Literature 1).

CITATION LIST

Patent Literature {PTL 1} Japanese Unexamined Patent Application, Publication No. 2020-124541

Non-Patent Literature {NPL 1} ZHOU, Tinghui et. al, "Unsupervised Learning of Depth and Ego-Motion from Video", 2017 IEEE Conference on Computer Vision and Pattern Recognition

SUMMARY OF INVENTION

Technical Problem

In the case of Patent Literature 1, it is necessary to provide the endoscope with a laser module that radiates the laser light for taking measurements. Accordingly, in order to measure the dimensions of the imaging subject, special equipment, such as a stereo optical system or a laser module, is required, and thus, it is not possible to measure the dimensions of an imaging subject by using a general monocular endoscope used in normal examination or treatment.

Three-dimensional reconstruction performed by using a monocular endoscope, as disclosed in Non-Patent Literature 1, is merely the reconstruction of a relative three-dimensional shape, and thus, it is not possible to acquire the absolute dimensions of an imaging subject.

In the case of an endoscope having a contrast autofocus function for automatically adjusting the focal position by moving an autofocus (AF) lens, it is possible to estimate the relationship between relative dimensions of three-dimensional information and absolute dimensions thereof from the imaging-subject distances by measuring the imaging-subject distances on the basis of the AF lens position at which the image contrast reaches a peak.

However, a measurement range in which the imaging-subject distances can be measured by utilizing contrast AF is restricted by the movable range of an AF lens. For example, in the case in which an AF lens position at which the image contrast reaches a peak is present in the movable range, it is possible to estimate the imaging-subject distances on the basis of the peak (see FIG. 5A). On the other hand, in the case in which an AF lens position at which the image contrast reaches a peak is not present in the movable range, it is difficult to estimate the imaging-subject distances on the basis of the image contrast (see FIG. 5B). In particular, in the case of a compact optical system, because the movable range of an AF lens is small, the measurement range for the imaging-subject distances is small.

The present invention has been conceived in light of the above-described circumstances, and an object thereof is to provide an image processing apparatus, an image processing method, and a recording medium, with which it is possible to measure the dimensions of an imaging subject from an image acquired by a general monocular endoscope regardless of the imaging-subject distances.

Solution to Problem

An aspect of the present invention is an image processing apparatus to which an image set consisting of a plurality of time-series images acquired by means of an endoscope is input, wherein the endoscope is capable of automatically adjusting a focal position by means of a contrast autofocus method, the image processing apparatus comprising a processor, wherein the processor is configured to: reconstruct, by employing the image set, three-dimensional information of an imaging subject containing relative dimensions; estimate, by means of an estimator, imaging-subject distances from the image set by employing a learning parameter, wherein the learning parameter is determined by learning a learning data set, and the learning data set includes a plurality of learning images including images of imaging-subject distances outside a measurement range in which imaging-subject distances can be measured on the basis of contrast of the image and a position of an autofocus-lens, as well as correct imaging-subject distances for each of said plurality of learning images; calculate, on the basis of the imaging-subject distances estimated by the estimator and the imaging-subject distances in the three-dimensional information, a scale coefficient for converting relative dimensions of the three-dimensional information to absolute dimensions; convert the relative dimensions of the three-dimensional information to absolute dimensions by employing the scale coefficient; and output the three-dimensional information containing the absolute dimensions.

Another aspect of the present invention is an image processing method for processing an image set consisting of a plurality of time-series images acquired by means of an endoscope, wherein the endoscope is capable of automatically adjusting a focal position by means of a contrast autofocus method, the image processing method comprising: reconstructing, by employing the image set, three-dimensional information of an imaging subject containing relative dimensions, estimating, by means of an estimator, imaging-subject distances from the image set by employing a learning parameter, wherein the learning parameter is determined by learning of a learning data set and the learning data set includes a plurality of learning images including images of imaging-subject distances outside a measurement range in which imaging-subject distances can be measured on the basis of contrast of the image and a position of an autofocus-lens, as well as correct imaging-subject distances for each of said plurality of learning images, calculating, on the basis of the imaging-subject distance estimated by the estimator and the imaging-subject distances in the three-dimensional information, a scale coefficient for converting relative dimensions of the three-dimensional information to absolute dimensions, converting the relative dimensions of the three-dimensional information to the absolute dimensions by employing the scale coefficient, and outputting the three-dimensional information containing the absolute dimensions.

Another aspect of the present invention is a computer-readable non-transitory recording medium that stores an image processing program for processing an image set consisting of a plurality of time-series images acquired by means of an endoscope, wherein the endoscope is capable of automatically adjusting a focal position by means of a contrast autofocus method, the image processing program causing a computer to execute: reconstructing, by employing the image set, three-dimensional information of an imaging subject containing relative dimensions; estimating, by means of an estimator, imaging-subject distances from the image set by employing a learning parameter, wherein the learning parameter is determined by learning of a learning data set and the learning data set includes a plurality of learning images including images of imaging-subject distances outside a measurement range in which imaging-subject distances can be measured on the basis of contrast of the image and a position of an autofocus-lens, as well as correct imaging-subject distances for each of said plurality of learning images; calculating, on the basis of the imaging-subject distances estimated by the estimator and the imaging-subject distances in the three-dimensional information, a scale coefficient for converting relative dimensions of the three-dimensional information to absolute dimensions; converting the relative dimensions of the three-dimensional information to the absolute dimensions by employing the scale coefficient; and outputting the three-dimensional information containing the absolute dimensions.

DESCRIPTION OF EMBODIMENT

An image processing apparatus, an image processing method, and a recording medium according to an embodiment of the present invention will be described below with reference to the drawings.

Figure 1:
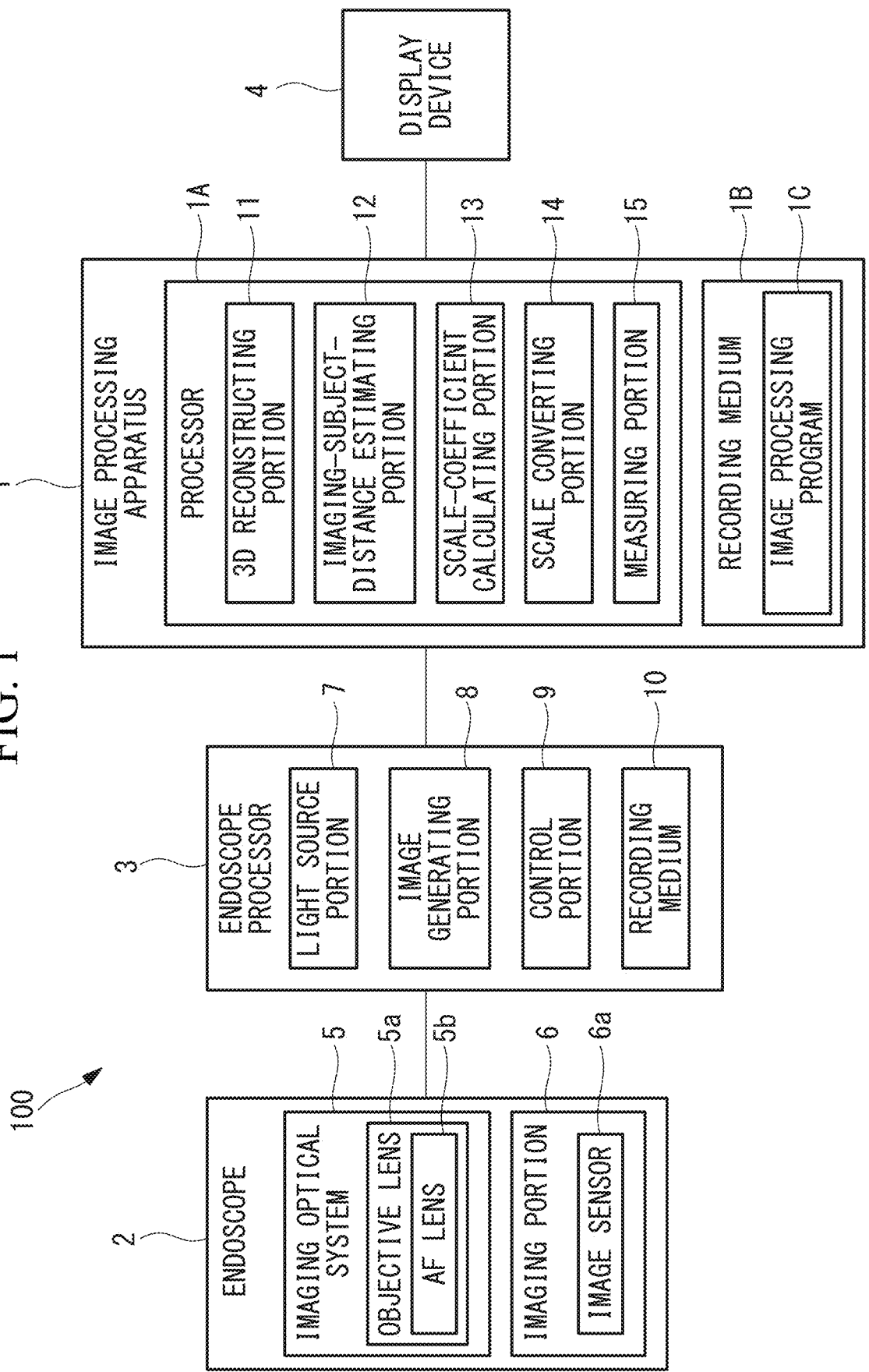
FIG. 1 is an overall configuration diagram of an endoscope system according to an embodiment of the present invention.

FIG. 1 shows an endoscope system 100 including an image processing apparatus 1 according to this embodiment. The endoscope system 100 includes an endoscope 2, an endoscope processor 3, the image processing apparatus 1, and a display device 4.

The endoscope 2 is a monocular endoscope that has only one objective lens 5a. The endoscope 2 includes an imaging optical system 5 and an imaging portion 6.

The imaging optical system 5 has the objective lens 5a and an actuator (not shown), and the objective lens 5a has an autofocus (AF) lens 5b that can be moved along an optical axis within a prescribed movable range. The actuator moves the AF lens 5b in accordance with focus control information from the endoscope processor 3, and thereby the position thereof is automatically adjusted to a position at which an imaging subject is in focus.

The imaging portion 6 has an image sensor 6a. The image sensor 6a captures an optical image of the imaging subject formed by the objective lens 5a and generates image signals of the imaging subject.

The endoscope processor 3 includes a light source portion 7, an image generating portion 8, a control portion 9, and a recording medium 10.

The light source portion 7 has a light source that emits illumination light for illuminating the imaging subject and provides the endoscope 2 with the illumination light.

The image generating portion 8 generates two-dimensional images from the image signals input to the endoscope processor 3 from the imaging portion 6. The image generating portion 8 may apply, as needed, processing, such as color correction processing and gamma correction processing, to the images. The generated images are sequentially output to the image processing apparatus 1 from the endoscope processor 3. Therefore, the plurality of time-series images are input to the image processing apparatus 1.

The control portion 9 has a processor and the recording medium 10 stores a control program for the control portion 9 to control the light source portion 7 and the imaging optical system 5.

The control portion 9 controls the focal position of the objective lens 5a by means of a contrast autofocus (AF) method. Specifically, the control portion 9 calculates the contrast in a prescribed detection region (for example, center region) in each image, generates focus control information on the basis of the contrast, and transmits focus control signals to the imaging optical system 5. Accordingly, the AF lens 5b is automatically moved to a position at which the detection region in each image is in focus.

The image processing apparatus 1 includes a processor 1A, such as a central processing unit, and a recording medium 1B.

The recording medium 1B is a computer-readable non-transitory recording medium and is, for example, a publicly known magnetic disk, optical disk, flash memory, or the like. The recording medium 1B stores an image processing program 1C for causing the processor 1A to execute the image processing method, described later.

The processor 1A executes the image processing method, thereby performing generation of a three-dimensional (3D) information of the imaging subject from the plurality of time-series images and measurement of the dimension of the imaging subject.

The display device 4 has a screen and displays the two-dimensional images input thereto from the image processing apparatus 1 on the screen. Furthermore, the display device 4 may display the 3D information of the imaging subject and other information such as the settings of the endoscope 2 or the like.

Next, the image processing apparatus 1 will be described in detail.

Figure 2:
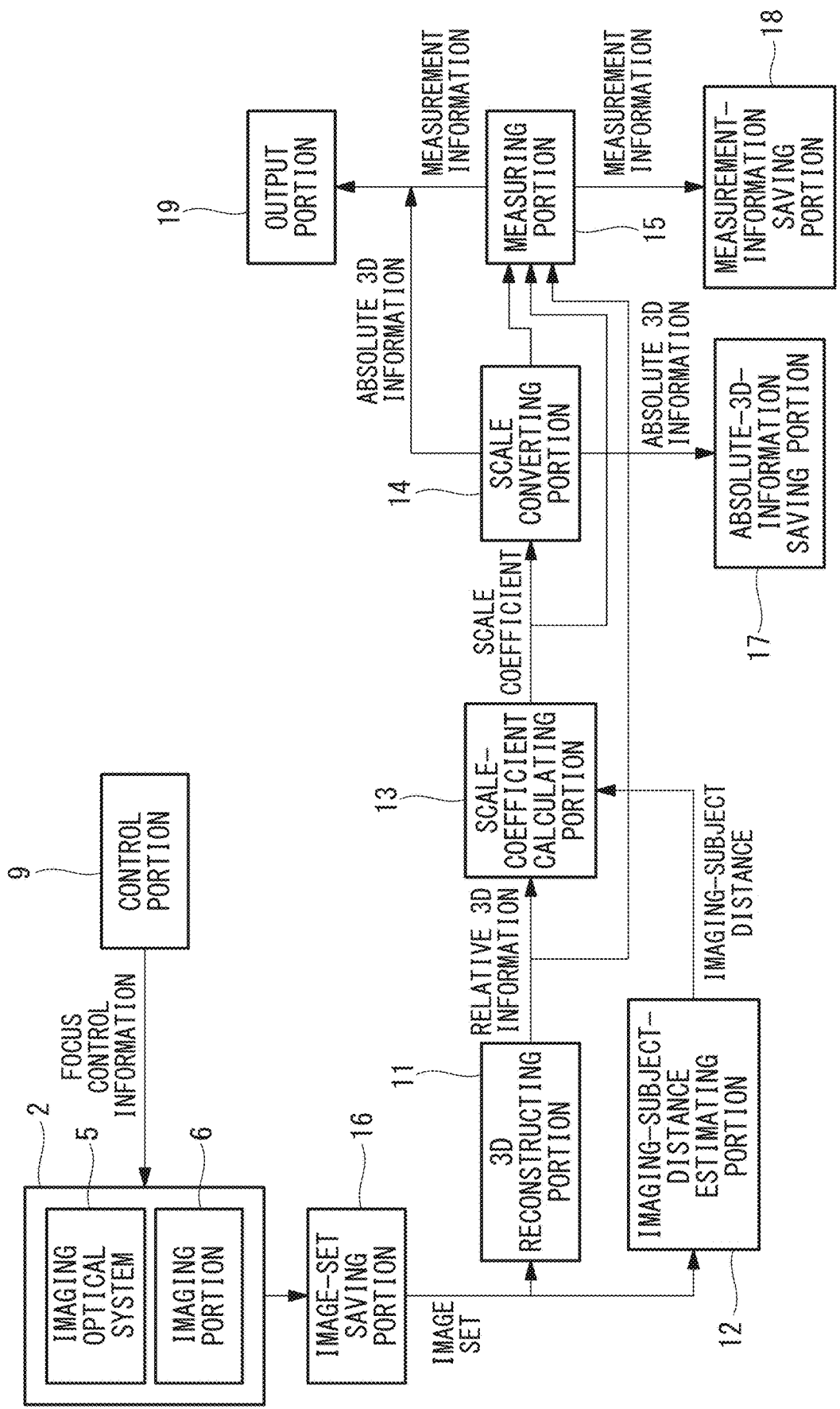
FIG. 2 is a functional block diagram of the endoscope system.

As shown in FIGS. 1 and 2, the image processing apparatus 1 has a three-dimensional (3D) reconstructing portion 11, an imaging-subject-distance estimating portion 12, a scale-coefficient calculating portion 13, a scale converting portion 14, a measuring portion 15, an image-set saving portion 16, an absolute-3D-information saving portion 17, a measurement-information saving portion 18, and an output portion 19.

Processing tasks performed by the 3D reconstructing portion 11, the imaging-subject-distance estimating portion 12, the scale-coefficient calculating portion 13, the scale converting portion 14, and the measuring portion 15, described later, are realized as functions of the processor 1A. The saving portions 16, 17, and 18 are constituted of the recording medium 1B or an arbitrary memory.

The image-set saving portion 16 at least temporarily saves an image set consisting of the plurality of time-series images input to the image processing apparatus 1 from the endoscope processor 3.

The 3D reconstructing portion 11 reads out the image set from the image-set saving portion 16 and generates the 3D information of the imaging subject from the image set. The 3D information is a 3D model of the imaging subject and contains relative dimensions of the imaging subject. In the following, the 3D information containing the relative dimensions will also be referred to as the relative 3D information. For example, the 3D reconstructing portion 11 generates the relative 3D information by converting the image set to point cloud data containing relative position data by means of a publicly known algorithm, such as the "Structure from Motion", by converting the point cloud data to polygon data having a mesh structure, and by applying texture data based on the images.

Figure 3A:
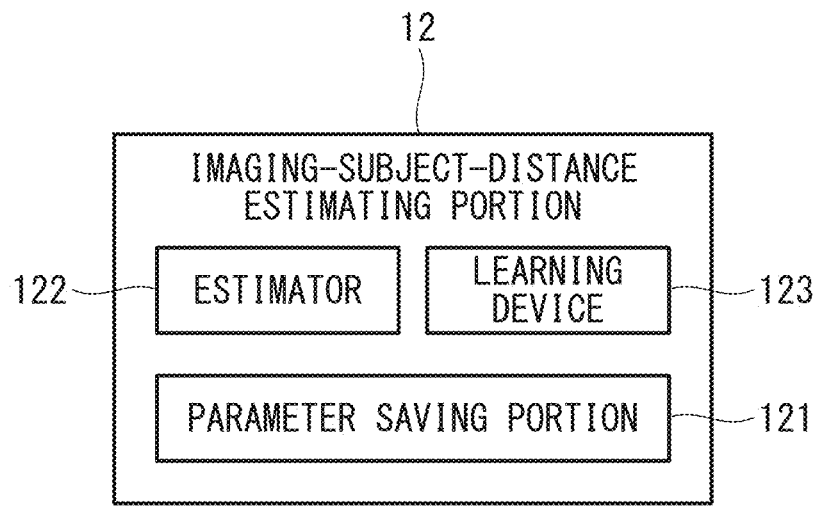
FIG. 3A is a block diagram of an example of an imaging-subject-distance estimating portion.
Figure 3B:
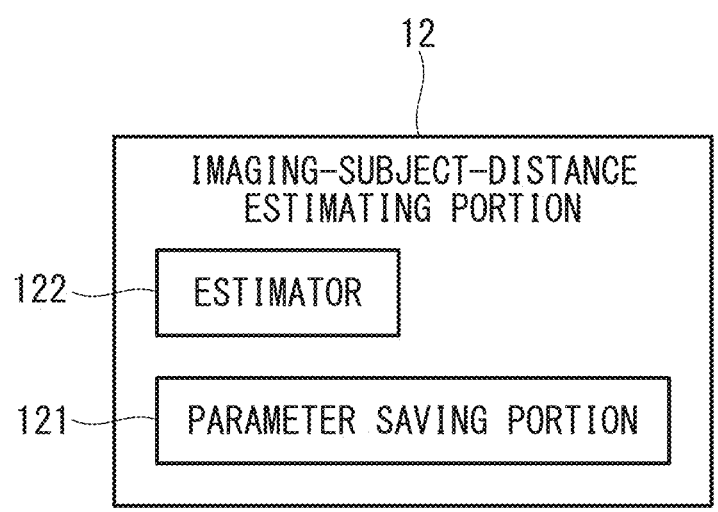
FIG. 3B is a block diagram of another example of an imaging-subject-distance estimating portion.

As shown in FIGS. 3A and 3B, the imaging-subject-distance estimating portion 12 has a parameter saving portion 121 that saves a learning parameter and an estimator 122 that estimates the imaging-subject distances from the image set by employing the learning parameter. The estimated imaging-subject distances are actual distances (absolute distances) from the objective lens 5a to the imaging subject in a direction along the optical axis.

The parameter saving portion 121 is the recording medium 1B or an arbitrary memory. The estimator 122 is a deep learning network and is stored in the recording medium 1B or other arbitrary memory. The learning parameter is a parameter for determining the imaging-subject distances from the image set and is determined by deep learning of a learning data set, described later.

The imaging-subject-distance estimating portion 12 loads the image set into the estimator 122 from the image-set saving portion 16, and estimates, by means of the estimator 122, the imaging-subject distances of at least two measurement points in each image included in the image set using the learning data.

As shown in FIG. 3A, the imaging-subject-distance estimating portion 12 may additionally have a learning device 123. The learning device 123 is a deep learning network having the same network structure as the estimator 122 and is stored in the recording medium 1B or other arbitrary memory. In this case, the learning device 123 determines the learning parameter by performing preliminary deep learning of the learning data set and the determined learning parameter is saved in the parameter saving portion 121 in advance. The learning is performed prior to using the image processing apparatus 1 in combination with the endoscope 2.

Figure 4:
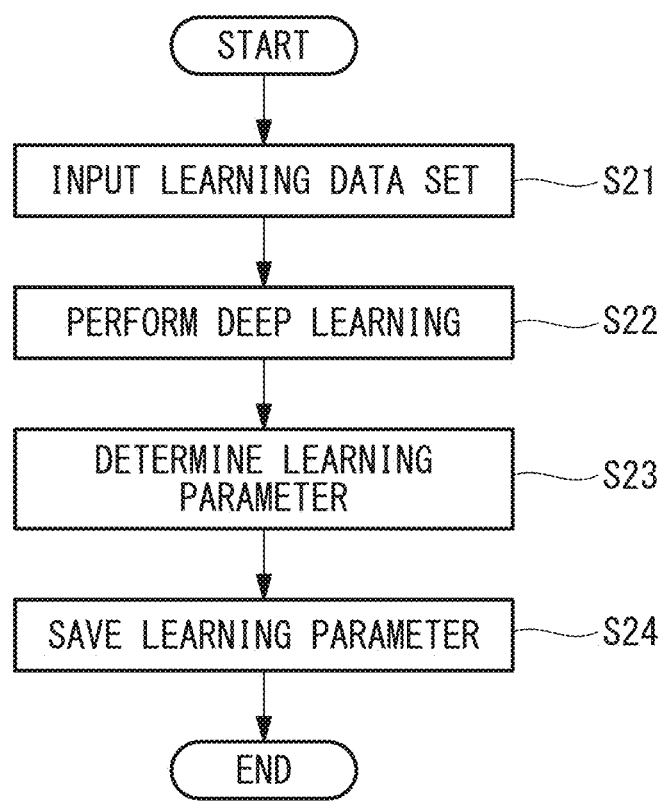
FIG. 4 is a flowchart for preliminary learning by a learning device.

As shown in FIG. 4, in the deep learning, the learning data set is input to the learning device 123 (step S21). The learning device 123 performs the deep learning of the learning data set (step S22) and determines the learning parameter (step S23). The determined learning parameter is saved in the parameter saving portion 121 (step S24).

As shown in FIG. 3B, the imaging-subject-distance estimating portion 12 need not have the learning device 123. In this case, the learning parameter may be determined as a result of the learning of the learning data set performed by an arbitrary learning device that is separate from the image processing apparatus 1, and the determined learning parameter may be saved in the parameter saving portion 121. The arbitrary learning device is a deep learning network having the same network structure as the estimator 122.

The learning data set contains numerous learning images and the correct imaging-subject distances for each of the numerous learning images. The learning images are images of various imaging-subject distances and the correct imaging-subject distance is the actual distance from the objective lens 5a to the imaging subject at the time of the learning image acquisition. The learning device 123 learns the relationship between the images and the image-subject distances by employing such an image data set and determines the learning parameter for estimating the imaging-subject distances from the images.

Figure 5A:
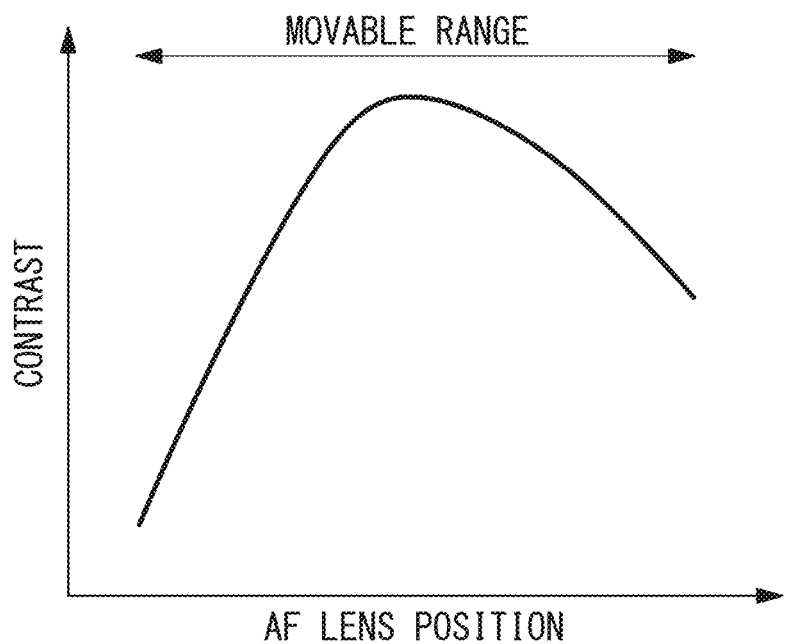
FIG. 5A is a diagram showing an example of the relationship between the AF-lens position and the image contrast.
Figure 5B:
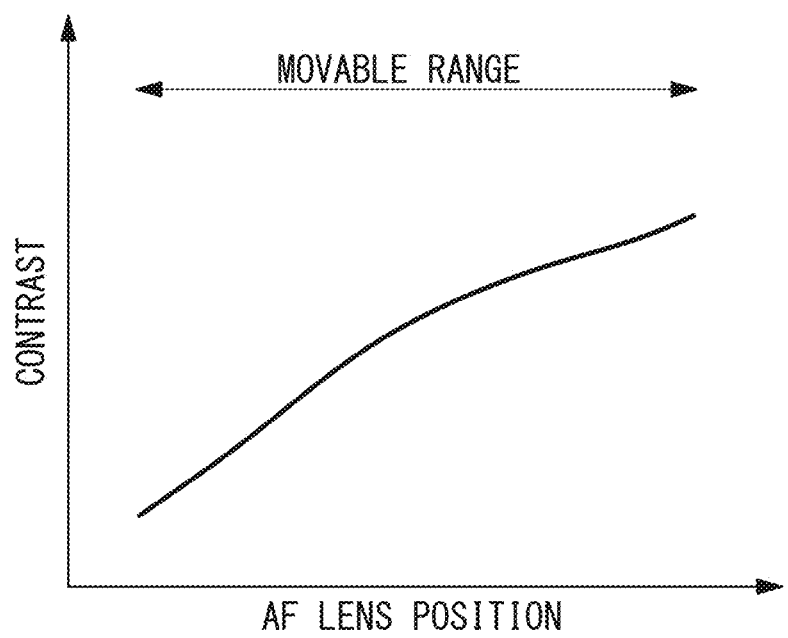
FIG. 5B is a diagram showing another example of the relationship between the AF-lens position and the image contrast.

FIGS. 5A and 5B show changes in the contrast in the images due to changes in the position of the AF lens 5b within the movable range.

Figure 6A:
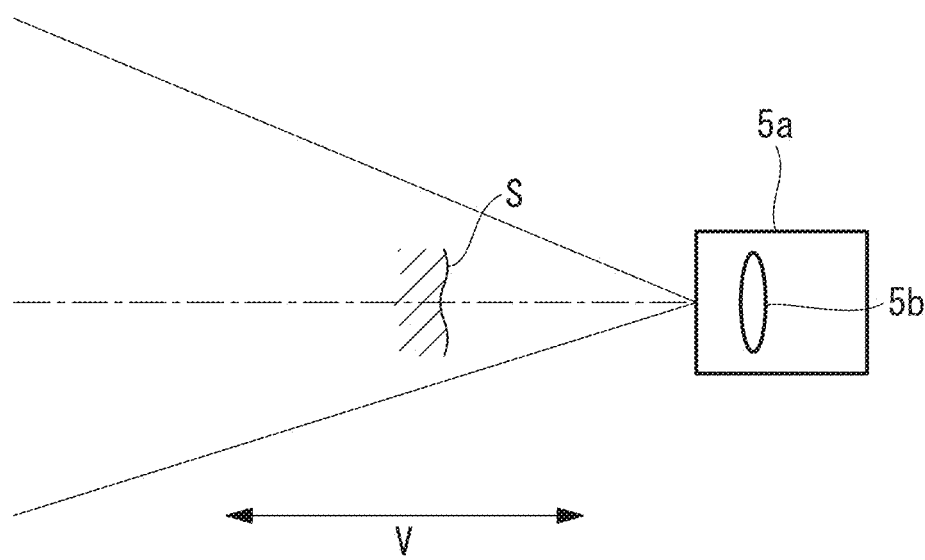
FIG. 6A is a diagram showing an example of position of the imaging subject with respect to a variable range of a focal point.

For example, in the case in which a portion of an imaging subject S corresponding to the detection region is disposed inside a variable range V of the focal point, as shown in FIG. 6A, the position of the AF lens 5b at which the imaging subject S is in focus and the contrast in the detection region in the image is at a peak is present in the movable range (see FIG. 5A). In this case, it is possible to measure the imaging-subject distances on the basis of the position of the AF lens 5b when the contrast is at the peak.

Figure 6B:
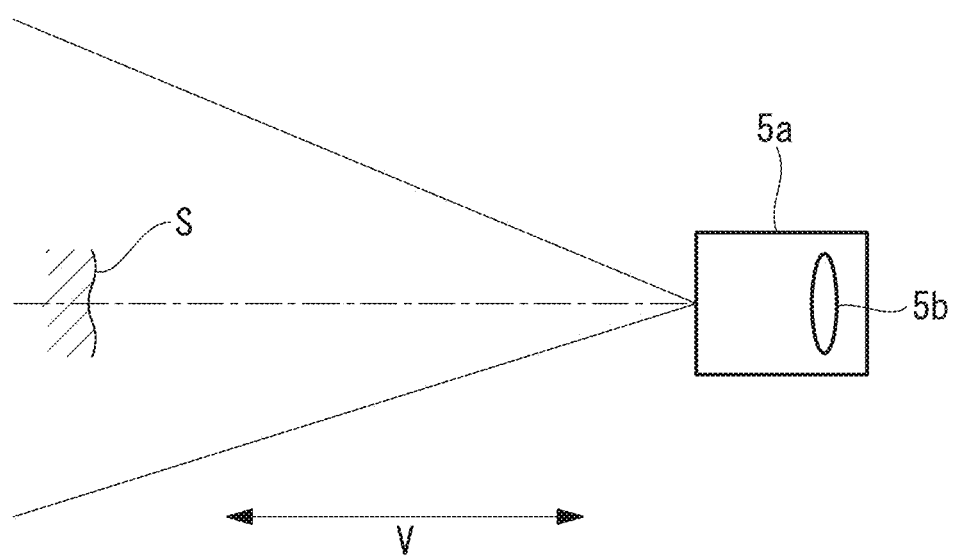
FIG. 6B is a diagram showing another example of position of the imaging subject with respect to the variable range of the focal point.

On the other hand, in the case in which the portion of the imaging subject S corresponding to the detection region is disposed outside the variable range V of the focal point, as shown in FIG. 6B, the position of the AF lens 5b at which the contrast in the detection region in the image is at a peak is not present in the movable range (see FIG. 5B). In this case, it is not possible to measure the imaging-subject distances on the basis of the contrast and the position of the AF lens 5b.

As above, the measurement range in which the imaging-subject distances can be measured by utilizing the contrast AF (in other words, on the basis of the contrast and the position of the AF lens 5b) is restricted in accordance with the movable range of the AF lens 5b.

The numerous learning images include images of imaging-subject distances, the range of which is greater than the measurement range in which the imaging-subject distances are measured by utilizing the contrast AF.

Specifically, the numerous learning images include images of various imaging-subject distances in the measurement range. The images of the imaging-subject distances in the measurement range are images of the imaging subject in which a portion thereof corresponding to the detection region is disposed inside the variable range V and images in which the detection region is in focus (see FIG. 6A).

Furthermore, the numerous learning images include images of various imaging-subject distances outside the measurement range. The images of the imaging-subject distances outside the measurement range are images of the imaging subject in which a portion thereof corresponding to the detection region is disposed outside the variable range V and images in which the detection region is out of focus (see FIG. 6B). These images may include images of various imaging-subject distances that are smaller than the measurement range and may include images of various imaging-subject distances that are greater than the measurement range. The images of the imaging-subject distances outside the measurement range are images of the imaging-subject distances in which the position of the AF lens $5b$ at which the contrast is at the peak is not present in the movable range (see FIG. 5B).

The scale-coefficient calculating portion 13 calculates relative distances which are imaging-subject distances in the relative 3D information corresponding to the imaging-subject distances estimated by the imaging-subject-distance estimating portion 12. Specifically, the scale-coefficient calculating portion 13 specifies two or more corresponding points in the relative 3D information, each of which corresponds to each of the two or more measurements points in the respective images and calculates the relative distances for the respective corresponding points in the relative 3D information. The estimated imaging-subject distances are the distances along the optical axis between two points, that is, the measurement point and the objective lens $5a$. The relative distances are the distances in the direction corresponding to the optical axis between the two points in the relative 3D information corresponding to the two points of the imaging-subject distances.

Next, the scale-coefficient calculating portion 13 calculates a scale coefficient for converting the relative dimensions of the 3D information to the absolute dimensions on the basis of the estimated imaging-subject distances and the relative distances. For example, the scale coefficient is a coefficient α by which a relative dimension ds is multiplied, as in equation (1) below, and is calculated as a ratio between the estimated imaging-subject distances and the relative distances. dt indicates the absolute dimensions of the imaging subject.

$$dt = \alpha \times ds \quad (1)$$

The scale converting portion 14 converts the relative dimensions of the relative 3D information to the absolute dimensions by employing the scale coefficient. For example, the scale converting portion 14 calculates the absolute dimensions dt from equation (1) by employing the coefficient a calculated by the scale-coefficient calculating portion 13. Accordingly, the 3D information of the imaging subject containing the absolute dimensions is generated. In the following, the 3D information containing the absolute dimensions will also be referred to as the absolute 3D information. The absolute 3D information is saved in the absolute-3D-information saving portion 17.

The measuring portion 15 executes, during the time when the measurement function of the image processing apparatus 1 is being executed, the measurement of the imaging-subject dimensions in the absolute 3D information. The dimensions measured by the measuring portion 15 are the actual dimensions (absolute dimensions) of the imaging subject. The measured dimension information is saved in the measurement-information saving portion 18.

The measurement function may be executed on the basis of an instruction input to the image processing apparatus 1 or the endoscope processor 3 by a user. In this case, the measuring portion 15 may measure the distance between two points specified by the user. For example, the user can specify, by using an arbitrary input device, two points in the two-dimensional image or the 3D information displayed on the display device 4.

The absolute 3D information generated by the scale converting portion 14 is output to the display device 4 from the output portion 19 together with the measured dimension information and is displayed on the display device 4.

Figure 7A:
FIG. 7A is an example of an image used in three dimensional reconstruction.
Figure 7B:
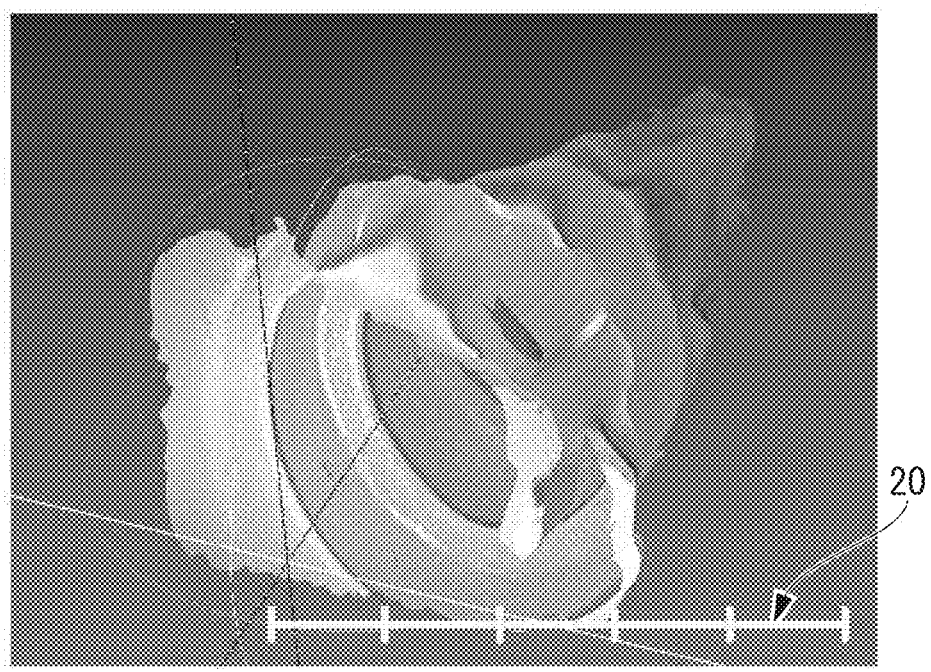
FIG. 7B is an example of absolute three dimensional information provided with a scale, displayed on a display device.

FIG. 7A shows a two-dimensional image used to generate the absolute 3D information, and FIG. 7B shows the absolute 3D information reconstructed by using the image in FIG. 7A. As shown in FIG. 7B, the absolute 3D information may be output to the display device 4 together with a virtual scale 20 representing the absolute dimensions. In this case, it is permissible not to execute the dimensional measurement by the measuring portion 15. The virtual scale 20 is, for example, a scale bar having 5-mm, 10-mm, or 20-mm scale. The virtual scale 20 may be superimposed on the image containing the absolute 3D information.

Next, the operation of the endoscope system 100 will be described.

Figure 8:
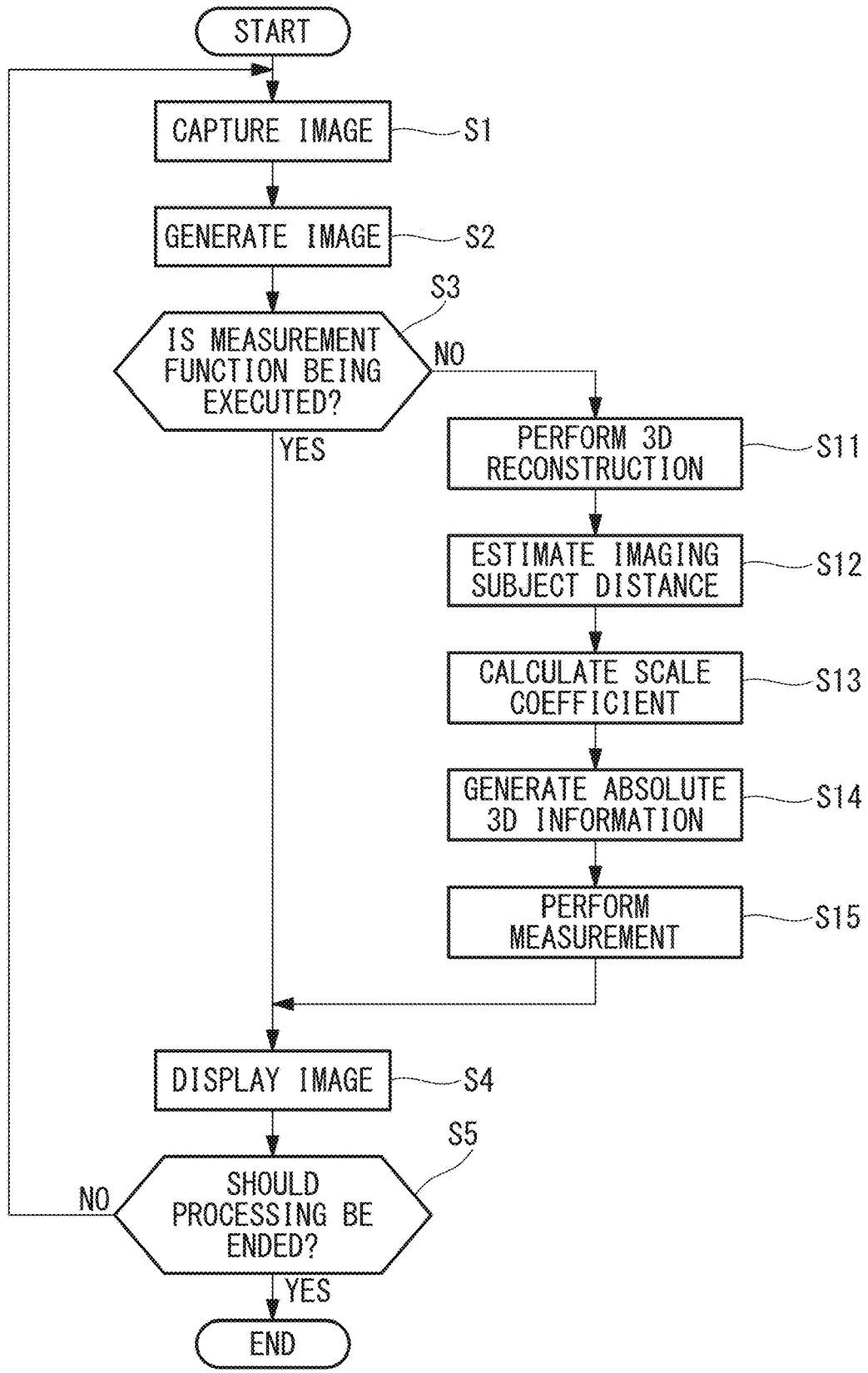
FIG. 8 is a flowchart of the operation of the endoscope system.

As shown in FIG. 8, after turning on the endoscope system 100, the imaging portion 6 captures images of an imaging subject (step S1), the image generating portion 8 generates images of the imaging subject (step S2), and the images are input to the image processing apparatus 1.

Next, whether the measurement function is being executed is checked (step S3).

In the case in which the measurement function is not being executed ("NO" in step S3), the two-dimensional images generated in step S2 are transmitted to the display device 4 from the endoscope processor 3 via the image processing apparatus 1, and the two-dimensional images are displayed on the display device 4 (step S4).

In the case in which the measurement function is being executed ("YES" in step S3), the processing for measuring the absolute dimensions of the imaging subject is executed (steps S11 to S15). Steps S11 to S15 correspond to the image processing method executed by the image processing apparatus 1.

The image processing apparatus 1 saves the input images in the image-set saving portion 16. After the image set required to generate the 3D information is accumulated in the image-set saving portion 16, the 3D reconstructing portion 11 reconstructs the relative 3D information of the imaging subject by employing the image set (step S11).

Next, the imaging-subject-distance estimating portion 12 estimates the imaging-subject distances from the image set (step S12). Specifically, the estimator 122 estimates the imaging-subject distance of at least two measurement points in each of the images by employing the learning parameter.

Next, the scale-coefficient calculating portion 13 calculates the scale coefficient for converting the relative dimensions of the relative 3D information to the absolute dimensions on the basis of the imaging-subject distances (step S13).

Next, the scale converting portion 14 converts the relative dimensions of the relative 3D information to the absolute dimensions by employing the scale coefficient, and the absolute 3D information is generated (step S14).

Next, the measuring portion 15 measures, in the absolute 3D information, the dimensions of the imaging subject, for example, the distance between two points specified by the user (step S15).

Then, the absolute 3D information to which information of the dimension of the imaging subject has been added is transmitted to the display device 4 from the image processing apparatus 1 and is displayed on the display device 4 (step S4).

Steps S1 to S4 and S11 to S15 are repeated until an ending instruction is input to the endoscope system 100 (step S5).

As has been described, with this embodiment, the imaging-subject distances, which are absolute dimensions, are estimated from an image set consisting of a plurality of two-dimensional images, and the scale coefficient for converting the relative dimensions to the absolute dimensions is calculated by employing the imaging-subject distances. The image set is obtained by using the general monocular endoscope 2. Therefore, it is possible to measure the absolute dimensions of the imaging subject from the two-dimensional images acquired by means of the general monocular endoscope 2 without requiring special equipment or work.

In addition, the imaging-subject distances are estimated by the estimator 122 by employing the learning parameter obtained by means of deep learning. In the deep learning, the images of the imaging-subject distances, the range of which is greater than the measurement range in which the imaging-subject distances are measured by utilizing the contrast AF, are employed as the learning images. As a result of employing such a learning parameter, even an imaging-subject distance that cannot be measured by utilizing the contrast AF can be estimated from the image set. Therefore, it is possible to measure the absolute dimensions of the imaging subject regardless of the imaging-subject distances.

As above, the embodiment of the present invention has been described in detail with reference to the drawings; however, specific configurations are not limited to the above-described embodiment and design alterations or the like within a range that does not depart from the scope of the present invention are also encompassed. In addition, the constituent elements indicated in the above-described embodiment and modifications can be configured, as appropriate, in combination.

REFERENCE SIGNS LIST 1 image processing apparatus
1A processor
1B recording medium
10 image processing program
2 endoscope
5a objective lens
5b autofocus lens
6a image sensor
122 estimator
123 learning device

The invention claimed is:

1. An image processing apparatus to which an image set consisting of a plurality of time-series images acquired by an endoscope is input, wherein the endoscope is configured to automatically adjust a focal position by a contrast autofocus method, the image processing apparatus comprising:
a processor comprising hardware,
wherein the processor is configured to:
reconstruct, by employing the image set, three-dimensional information of an imaging subject containing relative dimensions;
estimate imaging-subject distances from the image set by employing a learning parameter, wherein the learning parameter is determined by learning a learning data set, and the learning data set includes a plurality of learning images including images of imaging-subject distances outside a measurement range in which imaging-subject distances can be measured on the basis of contrast of the image and a position of an autofocus-lens, as well as correct imaging-subject distances for each of the plurality of learning images;
calculate, on the basis of the estimated imaging-subject distances and the imaging-subject distances in the three-dimensional information, a scale coefficient for converting relative dimensions of the three-dimensional information to absolute dimensions;
convert the relative dimensions of the three-dimensional information to absolute dimensions by employing the scale coefficient; and
output the three-dimensional information containing the absolute dimensions.

2. The image processing apparatus according to claim 1, wherein the plurality of learning images include images of imaging-subject distances in the measurement range and images of imaging-subject distances that are larger or smaller than the measurement range.

3. The image processing apparatus according to claim 1, wherein the plurality of learning images include images of imaging-subject distances in which the position of the autofocus-lens at which the contrast of the image is at a peak is not present in the movable range of the autofocus lens.

4. The image processing apparatus according to claim 1, wherein the processor is configured to load the learning parameter saved in advance and estimate the imaging-subject distances by employing the loaded learning parameter.

5. The image processing apparatus according to claim 4, wherein the processor is further configured to:
determine the learning parameter by causing a learning device to learn the learning data set, and
save the determined learning parameter in a saving portion.

6. The image processing apparatus according to claim 1, wherein the processor is further configured to measure a distance between two points specified in the three-dimensional information containing the absolute dimensions.

7. The image processing apparatus according to claim 6, wherein the processor is configured to output the three-dimensional information containing the absolute dimensions, to which the distance has been added.

8. An image processing method for processing an image set consisting of a plurality of time-series images acquired by an endoscope, wherein the endoscope is configured to automatically adjust a focal position by a contrast autofocus method, the image processing method comprising:
reconstructing, by employing the image set, three-dimensional information of an imaging subject containing relative dimensions,
estimating imaging-subject distances from the image set by employing a learning parameter, wherein the learning parameter is determined by learning of a learning data set, and the learning data set includes a plurality of learning images including images of imaging-subject distances outside a measurement range in which imaging-subject distances can be measured on the basis of contrast of the image and a position of an autofocus-lens, as well as correct imaging-subject distances for each of the plurality of learning images, calculating, on the basis of the estimated imaging-subject distance and the imaging-subject distances in the three-dimensional information, a scale coefficient for converting relative dimensions of the three-dimensional information to absolute dimensions, converting the relative dimensions of the three-dimensional information to the absolute dimensions by employing the scale coefficient, and outputting the three-dimensional information containing the absolute dimensions.

9. A computer-readable non-transitory recording medium that stores an image processing program for processing an image set consisting of a plurality of time-series images acquired by an endoscope, wherein the endoscope is configured to automatically adjust a focal position a contrast autofocus method, the image processing program causing a computer to execute:

reconstructing, by employing the image set, three-dimensional information of an imaging subject containing relative dimensions;

estimating imaging-subject distances from the image set by employing a learning parameter, wherein the learning parameter is determined by learning of a learning data set and the learning data set includes a plurality of learning images including images of imaging-subject distances outside a measurement range in which imaging-subject distances can be measured on the basis of contrast of the image and a position of an autofocus-lens, as well as correct imaging-subject distances for each of the plurality of learning images;

calculating, on the basis of the estimated imaging-subject distances and the imaging-subject distances in the three-dimensional information, a scale coefficient for converting relative dimensions of the three-dimensional information to absolute dimensions;

converting the relative dimensions of the three-dimensional information to the absolute dimensions by employing the scale coefficient; and outputting the three-dimensional information containing the absolute dimensions.

* * * * *